United States Patent
Nizam

(10) Patent No.: US 9,040,095 B2
(45) Date of Patent: May 26, 2015

(54) COLON CLEANSING OF RESIDUAL STOOL AND SECRETIONS DURING COLONOSCOPY

(75) Inventor: Rayees Nizam, Syracuse, NY (US)

(73) Assignee: GI INNOVATIONS, PLLC, Auburn, NY (US)

(*) Notice: Subject to any disclaimer, the term of this patent is extended or adjusted under 35 U.S.C. 154(b) by 0 days.

(21) Appl. No.: 13/502,344

(22) PCT Filed: Oct. 14, 2010

(86) PCT No.: PCT/US2010/052710
§ 371 (c)(1),
(2), (4) Date: Apr. 16, 2012

(87) PCT Pub. No.: WO2011/047178
PCT Pub. Date: Apr. 21, 2011

(65) Prior Publication Data
US 2012/0219642 A1 Aug. 30, 2012

Related U.S. Application Data

(60) Provisional application No. 61/251,344, filed on Oct. 14, 2009.

(51) Int. Cl.
*A61K 31/22* (2006.01)
*A61K 31/195* (2006.01)
*A61K 31/80* (2006.01)

(52) U.S. Cl.
CPC ............... *A61K 31/22* (2013.01); *A61K 31/195* (2013.01); *A61K 31/80* (2013.01)

(58) Field of Classification Search
USPC .................................................. 514/553, 740
See application file for complete search history.

(56) References Cited

U.S. PATENT DOCUMENTS

| | | |
|---|---|---|
| 5,310,537 A | 5/1994 | Illig et al. |
| 2004/0047910 A1 | 3/2004 | Beckett et al. |
| 2005/0004155 A1* | 1/2005 | Boyd et al. ..................... 514/282 |
| 2005/0129781 A1* | 6/2005 | Skiendzielewski et al. .. 424/601 |
| 2006/0276689 A1* | 12/2006 | Litscher et al. ............... 600/156 |
| 2007/0196322 A1 | 8/2007 | Pelham |
| 2008/0194456 A1 | 8/2008 | Podolsky |
| 2008/0213393 A1 | 9/2008 | Skiendzielewski et al. |
| 2008/0260682 A1 | 10/2008 | Rose et al. |

OTHER PUBLICATIONS

Yiengpruksawan et al. Gastroint. Endos. 1991, 37, 543-546.*
Dana-Farber (http://www.dana-farber.org/Health-Library/Understanding-upper-endoscopy-and-colonoscopy.aspx).*
American Society for Gastrointestinal Endoscopy, "Chromoendoscopy", Amer. Soc. for Gastoint. Endos., 2007, 66, 639-649.*
Tongprasert et al . World J. Gastroenterol. 2009, 15, 3032-3037.*
Nizam et al., "Endoscopic Dissolution of Phytobezoars Using Mucomist (Acetylcysteine)", The Journal of American Gastroenterology, vol. 91, No. 9, p. 1922. (1996). Abstract 156 Only.

* cited by examiner

*Primary Examiner* — Misook Yu
*Assistant Examiner* — Kauser M Akhoon
(74) *Attorney, Agent, or Firm* — Venable LLP; Michele V. Frank; Nancy J. Axelrod

(57) ABSTRACT

This invention relates, e.g., to a composition comprising two or more of: (a) N-acetylcysteine and/or (b) simethicone and/or (c) a docusate salt. In one embodiment of the invention, the amounts of (a) and/or (b) and/or (c) are effective, when the composition is administered into a colon of a subject undergoing colonoscopy, to cleanse a region of the colon in the visual field of the colonoscope so that the region contains no adherent stool or intestinal secretions obscuring the visual field. Methods for using this or other compositions of the invention, e.g. to cleanse the colon of a subject in order to enhance visualization of the colon during a colonoscopy, are also described, as are kits for carrying out methods of the invention.

5 Claims, No Drawings

COLON CLEANSING OF RESIDUAL STOOL AND SECRETIONS DURING COLONOSCOPY

This application is a National Stage Application of International Application No. PCT/US2010/052710 filed Oct. 14, 2010, which claims priority to Provisional Application No. 61/251,344, filed Oct. 14, 2009, the contents of both of which are hereby incorporated by reference in their entirety.

BACKGROUND INFORMATION

Colonoscopy is a medical procedure whereby a fiber optic instrument is introduced into the rectum and advanced into the colon (i.e., large intestine) for detailed examination of the colonic surface. The procedure is performed to diagnose and treat various conditions of the colon. It is the standard screening procedure for colon cancer, the second most common cause of cancer-related death in the U.S. and Canada. Colonoscopy is also performed for a variety of other reasons including investigating gastrointestinal and rectal bleeding, abdominal pain, change in bowel habits, or anemia; to diagnose inflammatory bowel disease; and to further evaluate abnormal gastrointestinal signs and symptoms.

Residual stool in the colon interferes with the quality of the screening, because the stool coats and covers the interior surface of the colon and thus impedes optimal visualization. In order to remove stool from the colon, the patient is normally directed to consume one or more laxatives the day before a colonoscopy, which essentially act as "purgatives."

Despite these efforts to clean the colon, a good percentage of patients still have stool residue and secretions left behind in the colon. These residual stool contents fill the colonic lumen and coat its surface, thus decreasing the quality of visualization and hence examination of the colon. Studies using large databases reveal that up to 23% of all colonoscopies are associated with suboptimal bowel cleansing and preparation. Suboptimal bowel preparation may decrease the frequency of complete examinations (i.e., advancing the instrument all the way to the cecum and visualizing the appendiceal opening) and may also increase the risk of complications, including increased time required to perform a colonoscopy, discomfort associated with the procedure, decreased detection rate of colon polyps, and in particular decreased detection of "flat lesions" and colon cancer. Suboptimal bowel preparation may also result in decreased time interval between screenings due to concerns about missed lesions.

When a gastroenterologist performs a colonoscopy, he/she is often faced with the following situation. Once the instrument has been introduced into the colon and the examination is in progress, the examiner encounters from a small to a large amount of stool and/or secretions in the colon. A diligent examiner may try to flush normal saline or water into the colon via the "working channel" of the colonoscope and clean the colon as much as possible to increase the quality of visualization. Cleaning the colon during each procedure can become time consuming. Due to the large volume of colonoscopies, an average gastroenterologist is usually very busy, typically performing several colonoscopies in a day. Time consuming, repetitive cleaning procedures can reduce the number of patients that undergo a colonoscopy in a given day.

DESCRIPTION

This invention relates, e.g., to compositions and methods which can be used to provide expedient colon cleansing during colonoscopy. In addition, other uses are also disclosed.

In one aspect, the invention provides compositions (e.g., pharmaceutical compositions, which comprise a pharmaceutically acceptable carrier). The compositions can comprise, for example, a) N-acetylcysteine (or another mucolytic agent); b) simethicone (or another antiflatulent that acts as a surfactant, decreasing the surface tension of gas bubbles, thereby dispersing and preventing gas pockets in the GI system); and c) a docusate salt, such as docusate sodium (or another stool softener). The mucolytic agent, surfactant/antiflatulent and stool softener can be present in amounts such that the composition is effective to cleanse stool from the colon of a subject (patient) prior to a colonoscopy. In one embodiment of the invention, the amounts of the components of the composition are such that the combination is effective, when administered into a colon through a colonoscope, in about six or fewer flushes (e.g., three or fewer flushes, or two or fewer flushes), to cleanse stool and intestinal secretions from the colon of a subject in a region of interest in the colon (e.g., within a visual field of the colonoscope) so that no adherent stool or intestinal secretions are visible (e.g., in the visual field of the colonoscope). In embodiments of the invention, the composition comprises: a) N-acetylcysteine: in an amount from about 0.5 to about 50 mL per 250 mL solvent (e.g., about 5 mL per 250 mL solvent), or from about 20 mg/L to about 20 g/L (e.g., about 2 g/L); b) simethicone: in an amount from about 0.12 to about 12 mL per 250 mL solvent (e.g., about 1.2 mL per 250 mL solvent), or from about 3 mg/L to about 3 g/L (e.g., about 600 mg/L); c) a docusate salt, such as docusate sodium: in an amount of from about 0.5 to about 50 mL per 250 mL solvent (e.g., about 5 mL per 250 mL solvent), or from about 2 mg/L to about 2 g/L (e.g., about 100 mg/L). Docusate sodium is sometimes referred to herein as "docusate."

The compositions can comprise a solvent, such as, for example, about 0.9 N saline (0.9 N saline is sometimes referred to herein as "normal saline") or water. The mucolytic agent can be, for example, N-acetylcysteine, dextran, 3% saline or a combination thereof. The surfactant/antiflatulent can be, for example, simethicone, dimethicone, activated methylpolysiloxane, polydimethylsiloxane or a combination thereof. The stool softener can be, for example, a docusate salt, such as docusate sodium, calcium, or potassium. The compositions can be formulated to be, for example, a powder for reconstitution, a concentrate for dilution, a working strength preparation of individual components for later combination, a solid oral dosage form, or a liquid oral dosage form. In one embodiment of the invention, because N-acetylcysteine degrades and loses activity within about 96 hours after a stock vial has been opened, if a composition of the invention is in a liquid form, the N-acetylcysteine is packaged separately from the other components and is added to them no more than about 96 hours before the composition is to be used.

In another aspect, the invention provides methods for cleansing the colon of a patient. The methods can comprise, for example, administering to the patient a composition disclosed herein. For example, the composition can comprise one or more of a) N-acetylcysteine and/or b) simethicone and/or c) a docusate salt, such as docusate sodium, provided that N-acetylcysteine or simethicone is not administered by itself. In one embodiment of the invention, the amounts of a), b) and c) are effective to cleanse stool from the colon of a patient prior to a colonoscopy. In one embodiment of the invention, the amounts of a), b) and c) are such that they are effective, when administered into a colon through a colonoscope, in about six or fewer flushes (e.g., three or fewer flushes, or two or fewer flushes), to cleanse the colon of a subject so that a region of the colon that present in the visual field of a colonoscope contains substantially no adherent stool or intestinal secretions. Amounts of the components of the composition can be the amounts disclosed above. The composition can be, for example, administered rectally or orally. The composition can be administered by, for example, introducing the cleansing agent into the colon through a colonoscope (e.g., by injection of the composition into a channel of the colonoscope with a syringe). The method can include the steps of a) providing a container operably connected with a conduit, a pump and a flush catheter, and containing a composition disclosed herein; and b) operating the pump; thereby administering the composition. Administering the composition can take place before the day of the patient's colonoscopy, on the day of the patient's colonoscopy or simultaneously with the patient's colonoscopy.

Another embodiment of the invention is a method for enhancing for enhancing the ability of a purgative (e.g., a polyethylene glycol (PEG), such as Golytly) to cleanse the colon of a subject, comprising orally administering to the subject, before, during, or after administering the purgative, a composition comprising one or more of:

a) N-acetylcysteine and/or
b) simethicone and/or
c) a docusate salt,
provide that N-acetylcysteine or docusate salt is not administered by itself, wherein the amounts of a), b) and c), are effective to enhance the amount of adherent stool and/or intestinal secretions in the colon of the subject.

The invention also provides methods for treating constipation in a patient in need thereof comprising administering to the patient a composition disclosed herein. The invention also provides methods for decreasing abdominal discomfort in a patient in need thereof comprising administering to the patient a composition disclosed herein. The composition can be, for example, administered orally.

In still another aspect, the invention provides kits. The kits can include, for example, a) a composition disclosed herein; and b) a container. The container can be, for example, a plastic container. The container can be suitable for (adapted to) administer the composition to a patient rectally or via a colonoscope. The container can also be adapted to be operably connected to a device, wherein the combination of container and device is adapted to administer the composition to a patient rectally or into the colon. In some embodiments, the kits can comprise more than one composition, each containing one or more of the active agents disclosed herein, as well as a container. The kit can be adapted for sequential administration of the compositions.

DESCRIPTION

As used herein, "surfactants/antiflatulents" are compounds and/or compositions that spread on the surface of liquids, forming a film of low surface tension, which can collapse foam bubbles. Such compounds can, for example, allow mucus-surrounded gas bubbles to coalesce and be expelled.

The compositions disclosed herein can be instilled/sprayed/introduced into the colon by any suitable device, such as, e.g., through a syringe or a spray catheter. The combination of components will effectively liquefy and clear excess stool, allay bubbles and foam, and generally clear out the colon to enhance visibility of potentially malignant lesions/polyps. Aside from pure stool, thick mucus secretions mixed with bile tend to coat the surface of the colon. Without wishing to be bound by any particular mechanism, it is suggested that a mucolytic agent such as N-acetylcysteine can exert mucolytic action through its sulfhydryl group, which opens up the disulfide bonds in the mucoproteins thus lowering the viscosity. It will break up the thick secretions, which stick to the colon surface and are otherwise very difficult to liquefy and siphon out. Published data on N-acetylcysteine shows (upon inhalation) mucus liquefaction occurs maximally within 5-10 minutes. Duration of mucus liquefaction is more than an hour. A composition of the invention will break up thick secretions and decrease the viscosity of the secretions thereby making it quite easy to draw them out of the colon. This will expedite and enhance the speed of cleaning unwanted secretions and stool from the colon while performing the colonoscopy.

The composition is a mixture of several components that together provide a desirable function in the colonoscopy procedure. For example, simethicone, when used in conjunction with other ingredients, provides the complete function of cleaning/flushing out the colon during a colonoscopy. When the components are combined to form a solution and then injected into the colon during the colonoscopy, they can remove froth, bubbles, and excess stool from the large intestine/colon, thereby making it easier to have a high quality examination during colonoscopy.

Compositions

In some embodiments, invention provides compositions. The composition be a solution comprising, for example, three elements:

A Mucolytic Agent.

An example of a suitable mucolytic agent is N-acetylcysteine (sometimes referred to herein as "acetylcysteine" or "NAC"). N-acetylcysteine can be provided in, for example, about 10% or about 20% (w/w) solutions. The term "about," as used herein, refers to plus or minus 10%. Other suitable mucolytic agents include, for example, dextran, 3% saline and saline solutions of concentrations greater than 3%. The mucolytic agent can, for example, act to break up the mucus that holds the stool together.

N-acetylcysteine can be used as a mucolytic agent. For example, it can be used as an adjunctive mucolytic therapy in patients with abnormal or viscid mucous secretions associated with acute and chronic broncho-pulmonary diseases, pulmonary complications of surgery and cystic fibrosis. It can also be used in diagnostic bronchial studies. Without wishing to be bound by any particular mechanism, it is suggested that it exerts its mucolytic effects through its free sulfhydryl group, which opens up the disulfide bonds in the mucoproteins and thus lowers the mucous viscosity. It can also act as an antidote, for example in acetaminophen toxicity, and presumably acts by providing substrate for conjugation with toxic metabolites. It is sold in the U.S. under the brand name Acetadote®.

N-acetylcysteine can also be used in the prevention of radio-contrast-induced renal dysfunction and distal intestinal obstruction syndrome (previously referred to as meconium ileus equivalent). Contraindications for acetylcysteine include hypersensitivity to acetylcysteine or any component of the formulations.

The mucolytic agent concentration in a composition of the invention can be, for example, about 0.5 to about 50 mL, about 1.25 to about 25 mL, about 2.5 to about 10 mL, or about 5 mL of a 20% (w/v) solution of mucolytic agent in 250 mL of a solvent such as normal saline or water. The mucolytic agent concentration in the composition can be, for example, up to or at least about 0.1, about 1.0, about 1.5, about 2, about 2.5, about 3, about 3.5, about 4, about 4.5, about 5, about 5.5, about 6, about 6.5, about 7, about 7.5, about 8, about 9, about 10, about 15, about 20, about 30, about 40, about 50 or more mL per 250 mL solvent, or about 0.2, 0.4, 1, 5, or 10 g/L. The mucolytic agent can be provided in a concentration of, for example, from about 100 mg to about 3000 mg, for example from about 1000 mg to about 1500 mg, of a mucolytic agent such as acetylcysteine per 250 mL solvent. N-acetylcysteine can be administered to the colon of an adult human by a method of the invention to an upper limit of about 50 gm per day.

A Surfactant/Antiflatulent:

Examples of suitable surfactants/antiflatulents include simethicone, dimethicone, activated methylpolysiloxane, polydimethylsiloxane, cetyl trimethylammonium bromide, sodium lauryl sulfate, sodium heptadecyl sulphate, an alkyl benzenesulphonic acid, sodium butylnaphthalene sulfonate, sulphosuccinate, carboxylic esters, carboxylic amides, ethoxylated alkylphenols and ethoxylated aliphatic alcohols, sorbitan esters, polyoxyethylene alkyl ethers and polyoxyethylene sorbitan fatty acid esters, Dow Corning Medical Antifoam AF and dextran. Other surfactants/antiflatulents suitable for use in the compositions disclosed herein are disclosed in U.S. Pat. No. 5,310,537 (issued May 10, 1994), which is hereby incorporated by reference in its entirety, particularly with reference to the surfactants/antiflatulents that are described therein. The surfactant/antiflatulent can, for example, spread on the surface of liquids, forming a film of low surface tension which collapses foam bubbles. As a result, it can allow mucus-surrounded gas bubbles to coalesce and be expelled.

Simethicone, for example, can be used as an antiflatulent because it decreases surface tension of gas bubbles, and thereby disperses and prevents gas pockets in the gastrointestinal tract. It can be used to relieve flatulence and functional gastric bloating, and post operative gas pains. It is sold under several brand names in the U.S., including Equalizer® Gas Relief (OTC); Gas-X® Extra Strength (OTC); Gas X® Maximum strength (OTC); Gas-X® (OTC); Infantaire™ Gas Drops (OTC); Mylanta® Gas Maximum Strength (OTC); Mylanta® Gas (OTC); Mylicon® Infants (OTC); Phazyme® Quick Dissolve (OTC); and Phazyme® Ultra Strength OTC). Its adverse side effects include loose stools. Contraindications include hypersensitivity to simethicone or any component of the formulation.

The surfactant/antiflatulent used can include, for example, 80 mg active agent per 1.2 mL dose, or about 60 g/L. The concentration of the surfactant/antiflatulent in the composition can be, for example, about 0.12 to about 12 mL, about 0.3 to about 6 mL, about 0.6 to about 2.4 mL, or about 1.2 ml in 250 mL of a solvent such as normal saline or water. The surfactant/antiflatulent concentration in the composition can be, for example, up to or at least about 0.01, about 0.05, about 0.08, about 0.1, about 0.15, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.5, about 3.0, about 3.5, about 4, about 5, about 10, about 12, about 15 grams or more surfactant/antiflatulent in 250 mL solvent. The upper limit for the administration of simethicone to the colon of an adult human by a method of the invention is about 2 gms/day.

A Stool Softener:

Examples of suitable stool softeners include, for example, docusate salts such as docusate sodium, potassium and calcium. The docusate sodium can be, for example, provided as a rectal enema in a concentration of about 83 mg/5 mL.

Docusate salts such as docusate sodium are sold under the following brand names in the U.S.: Colace®; Correctol®; D-S-S®; Diocto®; Docu-Soft; Docusoft-S™; DOK™; DOS®; Dulcolax® Stool Softener; Enemeez® Plus; Enemeez®; Fleet® Pedia-Lax™ Liquid Stool Softener; Fleet® Sof-Lax®; Genasoft®; Phillips'® Stool Softener Laxative [OTC]; Silace [OTC]; Surfak® [OTC]. They are sold in Canada under the brand names Apo-Docusate-Sodium®; Colace®; Colax-C®; Novo-Docusate Calcium; Novo-Docusate Sodium; PMS-Docusate Calcium; PMS-Docusate Sodium; Regulex®; Selax®; and Soflax™. They are sold internationally under the brand names Colace (CL); Coloxyl (AU); Cusate (TH); Dama-Lax (ES); Dioctyl (GB); Dipolaxan (PL); Docusaat FNA (NL); Docusoft (IL); Docusol (GB); Doslax (IN); Emtix (FI); Jamylene (FR); Klyx (FI, NL, NO, SE); Lambanol (IT); Laxadine (ID); Laxol (PL); Laxopol (PL); Molcer (GB); Norgalax (AE, BE, BH, CH, CY, DE, EG, GB, IE, IL, IQ, IR, JO, KW, LB, LU, LY, NL, OM, QA, RU, SA, SY, YE); Norgalax Micro-enema (GB); Purgeron (JP); Regutol (AE, BH, CY, EG, IL, IQ, IR, JO, KW, LB, LY, OM, QA, SA, SY, YE); Softon (HK); Soliwax (GB); Soluwax Ear Drops (MY, SG); Tirolaxo (ES); Wasserlax (ES); and Waxsol (AU, GB, IE)

Docusate salts can be provided in oral solid, liquid or soft gel capsules in 100 mg, 240 mg, 250 mg strengths; oral liquids in 50 or 150 mg per 15 mL strengths; rectal solution in 283 mg/5 mL strength; and/or as an oral syrup in 20 or 60 mg/5 mL strength. They can be used as a stool softener in patients who should avoid straining during defecation and those with constipation associated with hard, dry stools; and as prophylaxis for straining following myocardial infarction. Docusate salts can exert their effects by, for example, reducing surface tension of the oil-water interface of the stool, resulting in enhanced incorporation of water and fat allowing for stool softening.

Docusate salts should be taken with adequate fluids, and docusate syrup should be administered with 6-8 ounces of milk, juice, or infant formula to mask the bitter taste.

The stool softener stock solution of about 15 or 60 g/L can be included in a concentration of, for example, about 0.5 to about 50 ml, about 1.25 to about 25 mL, about 2.5 to about 10 mL, or about 5 mL per 250 mL of a solvent such as normal saline or tap water. The stool softener concentration in the composition can be, for example, up to or at least about 0.1, about 1.0, about 1.5, about 2, about 2.5, about 3, about 3.5, about 4, about 4.5, about 5, about 5.5, about 6, about 6.5, about 7, about 7.5, about 8, about 9, about 10, about 15, about 20, about 30, about 40, about 50 or more mL per 250 mL solvent, providing an end concentration of about 0.2 to about 2 g/L. The upper limit of docusate sodium that can be administered to the colon of an adult human by a method of the invention is about 500 mg to one gram in 24 hours.

The above components can be combined in an aqueous vehicle such as, for example, normal saline (0.9 N saline), tap water or distilled water. Because the colon is a contaminated organ it is generally not necessary to use a sterile solvent. In some embodiments, the composition comprises a mucolytic agent and a surfactant/antiflatulent, for example in an aqueous vehicle such as normal saline, tap water or distilled water. The composition can comprise a sctant/antiflatulent and a stool softener; or it can comprise a mucolytic agent and a stool softener. In some embodiments, the composition comprises a mucolytic agent, or more than one mucolytic agent. The composition can also comprise a surfactant/antiflatulent, or more than one surfactant/antiflatulent. Any such composition that achieves cleansing of the colon as described herein is contemplated as part of the invention.

In one embodiment of the invention, the composition further comprises a fibrinolytic agent that can break up the fibrin tangle of a blood clot, thereby dissolving blot clots. Suitable agents, and concentrations for using them, will be evident to a skilled worker. A composition of the invention that comprises a fibrinolytic agent can be particularly useful for, e.g., treating an upper GI bleed, such as an ulcer in the stomach.

Each of the components of a composition of the invention can be provided in pure form, mixed or dissolved in the solvent, or in a stock solution of, e.g., 1 g/L, 2 g/L, 3 g/L, 5 g/L, 10 g/L, 25 g/L, 50 g/L, 100 g/L, 200 g/L, 250 g/L, or higher or lower amounts depending on conventional factors such as solubility and stability. The end concentration in the working strength colonoscopic formulations will be lower than in the stock solutions due to dilution and may be diluted, e.g., 2, 5, 10, 50, 100, 200 or 500 fold. The end concentrations may thus be about 2 mg, 3 mg, 10 mg, 50 mg, 0.1 g, 0.2 g, 0.5 g, 1 g, 1.5 g, 2 g, 5 g, or 10 g/L, or more or less or in between these amounts.

The compositions disclosed herein can be effective in assisting cleansing of a colon prior to a colonoscopy. Human stool can be classified according to the Bristol Stool Scale. The form of the stool depends on the time it spends in the colon. The seven types of stool are:

Type 1: Separate hard lumps, like nuts (hard to pass)
Type 2: Sausage-shaped, but lumpy
Type 3: Like a sausage but with cracks on its surface
Type 4: Like a sausage or snake, smooth and soft
Type 5: Soft blobs with clear cut edges (passed easily)
Type 6: Fluffy pieces with ragged edges, a mushy stool
Type 7: Watery, no solid pieces. Entirely liquid.

Types 1 and 2 indicate constipation, with 3 and 4 being the "ideal stools" (especially the latter), as they are the easiest to pass. Types 5-7 further tend towards diarrhea or urgency.

For a careful and detailed examination of the colon, the colonic mucosa (surface lining) has to be exposed, and optimally it will be exposed substantially completely. If the surface is covered with mucus, stool, bile or other substances, the examiner cannot state with confidence that the entire colon was carefully examined. Pockets of secretions and stool puddles are dispersed throughout the colon. Furthermore, despite complete evacuation of the stool content of the colon, intestinal juices are still being continually produced and may interfere with the examination. Thus, even where the colon has been thoroughly cleansed, there is ongoing passage from the small intestine into the colon of "viscous bile", small intestinal juice "succus entericus" and colonic mucus production which coats the surface of the colon. These secretions are sometimes referred to herein as "intestinal secretions." In a dehydrated patient the secretions are relatively dry and thick, and thus they stick to the colon surface. Even when water is flushed into the colon, it is quite difficult to wash off the dried secretions, as they can become firmly stuck to the colonic surface. Without wishing to be bound by any particular theory, the mucus threads may be a factor that keeps these "thick and dry secretions" stuck to the wall. According to the methods, devices, kits and compositions disclosed herein, the combination of a mucolytic agent, surfactant and stool softener can soften and break these secretions, which can then be suctioned away, resulting in a clean surface to examine. As used herein, "cleanse" encompasses cleaning the colon such that the colon is not only free of stool but also of intestinal secretions, which are often wet, thick and desiccated and which can coat the colonic surface. Optimally, a cleansed colon is substantially completely free of stool and other secretions. By "substantially free of stool and other secretions" is meant that a region of interest of the colon (e.g., a region that is visible in the visual field of a colonoscope) contains little if any visible adherent stool or intestinal secretions. Ideally, no such items that block the field of vision are present, although a few such items may be present in certain circumstances (e.g., at least about 95%, 99%, or 99.9% of the area may be free of such items). In one embodiment of the invention, the administration of a cleansing solution through a colonoscope in three or fewer (e.g., two or fewer) flushes is sufficient to render the cleansed colon substantially free of stool or intestinal secretions that are visible in the visual field of a colonoscope. This degree of cleansing cannot be achieved by using water or saline alone, instead of a composition of the invention. When syringes are used to flush the colon, the volume of liquid is generally about 60-200 ml. When a foot pedal/pump apparatus, as described elsewhere herein, is used, the volume of liquid is generally about 5-6 syringes full, wherein each syringe holds about 60 ml. of liquid.

The composition can be provided, for example, in powder form, to maximize shelf life and enable the mixture to be prepared when it is needed. It can be mixed into solution form with added saline. The composition can be, for example, readily soluble, and thus reconstitution generally requires normal mixing. Alternatively, the compositions disclosed herein can be kept in liquid form. Additionally, the compositions can be provided as a concentrate for dilution, as a working strength preparation of individual components for later combination, or in solid or liquid oral dosage forms.

The compositions in powder form can be packaged in, for example, a plastic container similar to a one-gallon milk container, and can be, for example, transparent. Other packaging materials can also be used, as would be understood by a person of ordinary skill in the art.

The compositions disclosed herein can be stored and used in endoscopy suites worldwide. They can be, for example, instilled into the colon during a colonoscopy to enhance cleaning of the colon and improve the quality of examination. The product can also be used the day before the colonoscopy to assist with colon cleansing prior to the colonoscopy.

The compositions can be prepared for oral administration. Concentrations for the individual components would be the same in a composition for oral administration as in a composition for rectal administration.

Devices

In some embodiments, the invention provides devices. The device can comprise, for example, a colonoscope modified so as to deliver cleansing agent into the colon through the working channel of the colonoscope. The device can also comprise, for example, a "pump and catheter" device. The "pump and catheter" device comprises a container, a pump operably connected to the container and/or conduit; a conduit operably connected to the container and/or the pump; and a flushing catheter operably connected to the conduit. To use the "pump and catheter" device, the "cleansing agent" is placed in a container; the container is connected to a pump with a conduit; and the pump sucks up and flushes the fluid into the colon via a spray catheter. The pump can be controlled with a foot pedal. (The tubing coming from the pump is connected to an opening in the colonoscope. The fluid is dumped into the colonoscope channel with force and it comes out of the colonoscope like a jet.)

A device that is suitable for use with the invention employs a pump unit operable with a foot switch. The device also has a water bottle holder and a pump head. The device can be connected to suitable tubing, for example sterile irrigation tubing, which is also connected to a filled fluid bottle filled with, for example, a cleansing composition disclosed herein, and a backflow valve. The tubing can also be connected to, for example, an endoscope. The device is configured in such a way as to permit introduction of the cleansing composition intracolonically into the patient. Suitable parts for the device are sold under the trade name EndoGator™, for example the EndoGator™ Irrigation Pump, Pump Unit, Footswitch, Water Bottle Holder, Pump Head and Irrigation Tubing. Other suitable parts can be obtained from, e.g., Fujinon.

For example, the irrigation pump can be put on a flat surface near the endoscope, or near the floor. The footswitch is attached to the appropriate port on the pump. The shaft hole on a pump head unit is aligned with the shaft on the pump. The pump head is rotated and pushed until it sets flush against the pump, and then rotated until it is tightly secured. The water bottle holder is attached to the pump. A bottle of fluid, for example cleansing composition, is opened and placed into the water bottle holder, and irrigation tubing is attached to the bottle. The pump head is opened to permit fluid flow. The flow rate is adjusted and the pump is then operated. Other arrangements can also be used, in conjunction with a composition or method of the invention, as will be evident to a skilled worker.

Methods

In some embodiments, the invention provides methods for using the compositions disclosed herein. For example, the invention provides methods for cleansing the colon of a patient. These methods can include, for example, administering to the patient one or more of the compositions disclosed herein. Administering the composition can comprise, for example, introducing the cleansing agent into the colon through a colonoscope, for example through the colonoscope's "working channel." For example, a large (e.g., 60 cc) syringe can be filled with the composition, either from a bottle containing the composition or a receptacle, such as a kidney tray, and the composition can then be injected via the "working channel" of the colonoscope. This channel is often used to flush water/sterile water/saline into the colon to wash the colon. Simethicone with sterile water can also be used to clean the colon. In other embodiments, administering the composition can occur through a device comprising a container containing a composition disclosed herein; a pump operably connected to the container and/or conduit; a conduit operably connected to the container and/or the pump; and a flushing catheter operably connected to the conduit. This method can involve administering the composition before the day of the patient's colonoscopy, on the day of the patient's colonoscopy, or simultaneously with the patient's colonoscopy. The composition can also be administered orally. In one embodiment of the invention, the composition is administered in conjunction with a purgative such as Golytly (e.g., before, with, or after the purgative has been administered), as an oral formulation, such as a liquid, a pill, a time-released cap, etc.

In some embodiments, the methods comprise treating constipation in a patient in need thereof comprising administering to the patient one or more of the compositions disclosed herein. In some embodiments, the methods comprise decreasing abdominal discomfort in a patient in need thereof comprising administering to the patient one or more of the compositions disclosed herein.

In some embodiments, the invention provides methods for treating gastric bezoars in a patient in need thereof. The methods can comprise, for example, administering a composition disclosed herein to a patient. The composition can be administered orally, for example as one or more oral solutions, soft gels, tablets or capsules. The dosage forms can, for example, dissolve in the stomach and subsequently assist in liquefying the bezoar. Administering the composition can also comprise, for example, introducing the cleansing agent into the stomach through a gastroscope, for example through the gastroscope's "working channel." For example, a large (e.g., 60 cc) syringe can be filled with the composition, either from a bottle containing the composition or a receptacle, such as a kidney tray, and the composition can then be injected via the "working channel" of the gastroscope. Treatment of gastric bezoars may be accomplished in one administration, or several administrations over days, weeks or months may be required. The patient can be, for example, a human or an animal, such as a dog or another animal that is susceptible to developing bezoars.

Gastric bezoars result from the accumulation of foreign ingested material in the form of masses or concretions. Bezoars are rare, being found in less than 1 percent of patients undergoing upper gastrointestinal endoscopy. Bezoars grow by the continuing ingestion of food rich in cellulose and other indigestible materials such as hair, cotton, and tissue paper, matted together by protein, mucus, and/or pectin. Properties of the specific ingested material and some degree of gastric dysfunction also contribute. Bezoar formation is rare in healthy subjects.

Bezoars are classified according to their composition. The major types are phytobezoars, trichobezoars, and pharmacobezoars. Phytobezoars, composed of vegetable matter, are the most common type of bezoar. The diospyrobezoar (persimmon fruit) accounts for the majority of cases. Lupini beans, used by healers to treat arthritic pain, have also formed a bezoar. Trichobezoars, composed of hair, usually occur in young women with psychiatric disorders. Trichotillomania (hair pulling) and trichophagia (hair eating) usually precede trichobezoar formation. Pharmacobezoars, composed of ingested medications, have become increasingly recognized. Examples of medications that have been associated with bezoars include extended release nifedipine, theophylline, enteric-coated aspirin, sodium alginate, and sucralfate. Bezoars composed of a variety of other substances have been described. These include milk curd, tissue paper, shellac, fungus, Styrofoam cups, cement, and vinyl gloves.

It was recognized in 1938 that most patients with bezoars had undergone gastric surgery, implying that there are underlying anatomic and functional abnormalities. More recent studies have shown that 70 to 94 percent of patients have a history of gastric surgery and 54 to 80 percent have undergone vagotomy and pyloroplasty. It was initially thought that the most common functional abnormality found in patients with bezoars was delayed gastric emptying. However, some studies have found that many patients have normal or accelerated gastric emptying. This implies that the pathogenesis of bezoar formation is more complex than initially thought and involves other factors such as alterations in the production of acid, pepsin, and mucus, and impairments in the grinding mechanism and the interdigestive migrating motor complex.

Bezoars are usually discovered as an incidental finding in a patient with nonspecific symptoms. Abdominal radiograph with or without barium, abdominal ultrasound, or CT scan may show the bezoar as mass or a filling defect. The current gold standard for diagnosis is upper gastrointestinal endoscopy. It provides direct visualization of the bezoar and allows sample taking and therapeutic intervention. It is important to sample the bezoar for analysis since it may be difficult to determine the composition based upon appearance.

Therapy for bezoars should be tailored to the composition of the concretion and to the underlying pathophysiologic process. Available treatment methods include chemical dissolution, endoscopy, and surgery. Endoscopic removal involves fragmenting the bezoar with water jet, direct suction through a large channel (6 mm) endoscope, forceps, and snares and then clearing the fragments with the endoscope, Ewald tube, or passive passage through the gastrointestinal tract.

The patient according to the present invention is a mammal, such as a human, which is diagnosed with one of the diseases, disorders or conditions described herein, or alternatively is predisposed to at least one type of the diseases, disorders or conditions described herein. The compositions of the present invention can be administered to any mammal in need of the composition that can experience the beneficial effects of the compounds of the invention. Any such mammal is considered a "patient." Such patients include humans and non-humans, such as humans, domestic and farm animals, and zoo, sports, or pet animals, such as dogs, horses, cats, cows, etc. The patient can be a man or a woman.

"Treat" refers to preventing, curing, reversing, attenuating, alleviating, minimizing, suppressing or halting at least one of the symptoms or deleterious effects of the diseases, disorders or conditions described herein. Treatment refers to both therapeutic treatment and prophylactic or preventative measures. Those in need of treatment include those already with the disorder as well as those in which the disorder is to be prevented. Hence, the patient to be treated herein may have been diagnosed as having the disorder or may be predisposed or susceptible to the disorder.

In some embodiments, the invention provides methods for making the compositions disclosed herein. The methods for making can comprise, for example, preparing any of the following: a ready-to-use, working strength composition; a powder for reconstitution; a concentrate for dilution; or separate solutions, each comprising a component of the overall composition at appropriate concentration, for later combination.

The compositions administered according to the methods disclosed herein can comprise a mucolytic agent, a surfactant/antiflatulent and a stool softener in a single composition. Additionally, the mucolytic agent, surfactant/antiflatulent and stool softener can each be included in a separate composition to be administered sequentially to the patient. The methods can comprise sequential administration of the mucolytic agent and the surfactant/antiflatulent; or sequential administration of the mucolytic agent and stool softener; or sequential administration of the surfactant/antiflatulent and stool softener. The methods can comprise sequential administration of two compositions, the first composition containing any two of the active agents, and the second composition containing the third active agent. For any method involving sequential administration, the order of administration is not critical. In some embodiments, the separate compositions each comprising one or more of the active agents can be mixed in a receptacle, for example a bottle or a kidney dish, and then administered to the patient.

If a gastroenterologist encounters a poorly prepped colon during a colonoscopy examination, it becomes difficult to examine the colon in detail. compositions disclosed herein can be intended to be instilled into the colon via a colonoscope during a colonoscopy. It can, for example, cleanse the colon of excess stool and secretions, thus enhancing visualization and analysis of the colon and making it easier to identify colonic polyps/neoplasms (tumors).

The inventors have surprisingly discovered that that the compositions disclosed herein can be used for subverting residual stool during a colonoscopy, for example by liquefaction and softening of stool via introducing chemical agent(s), which in turn facilitates the cleansing of the colon. The compositions disclosed herein can, for example, disintegrate the stool and make it easier to remove the colonic contents during a colonoscopy. The compositions, methods and other embodiments disclosed herein can thus improve the quality of a colonoscopy by increasing the quality if visualization of the colon, which in turn can decrease the chances of missing polyps, in particular the "flat lesion" in the colon. The compositions, methods and other embodiments disclosed herein can also decrease the time of examination, thus increasing the efficiency of an endoscopy center and allowing more patients to be examined by a physician in a given day. They can also avoid the need to decrease the time between examinations. Such decreasing may be done out of concerns that lesions, polyps or masses were missed during a colonoscopy. The compositions, methods and other embodiments disclosed herein can also decrease complications of a colonoscopy.

Kits

In still another aspect, the invention provides kits. The kits can include, for example, a) a composition disclosed herein; and b) a container. The container can be, for example, a plastic container. The container can be, for example, adapted to administer the composition to a patient rectally and/or into the colon. The container can also be adapted to be operably connected to a device, wherein the combination of container and device is adapted to administer the composition to a patient rectally and/or to the colon. In some embodiments, the kits can comprise more than one composition, each containing one or more of the active agents disclosed herein, as well as a container. The kit can be adapted for sequential administration of the compositions.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, rectally or intracolonically. The compositions can be administered in the form of an enema, for example a tap water enema. In such an enema, from about 100 mL to about 3 L, for example from about 250 mL to about 1.5 L, or about 250, 500, 750, 1000, 1250 or 1500 mL or more of the composition can be administered.

The compositions can be administered intracolonically, for example during a colonoscopy through the colonoscope's "working channel." For example, a large (e.g., 60 cc) syringe can be filled with the composition, and the composition can then be injected via the "working channel" of the colonoscope. This channel is often used to flush water/sterile water/saline into the colon to wash the colon. When administered using this method, from about 10 to about 2,000 mL, for example from about 100 to about 1500 mL, or from about 250 to about 1000 mL, or from about 100, 150, 200, 250, 300, 350, 400, 450, 500, 550, 600, 650, 700, 750, 800, 850, 900, 950, 1000, 1100, 1200, 1300, 1400, 1500 mL or more of the composition can be administered.

The compositions can be administered orally, for example before the day of a patient's colonoscopy or on the day of a colonoscopy. When administered orally, from about 10 to about 2,000 mL, for example from about 100 to about 1500 mL, or from about 250 to about 1000 mL, or from about 100, 150, 200, 250, 300, 350, 400, 450, 500, 550, 600, 650, 700, 750, 800, 850, 900, 950, 1000, 1100, 1200, 1300, 1400, 1500 mL or more of the composition can be administered. The composition can be administered orally, for example to cleanse the patient's colon, or to relieve constipation or abdominal discomfort. Other uses will be apparent to a person of ordinary skill in the art. The solvent used in an oral composition can be tap water, distilled water or saline, for example normal saline, or any other solvent disclosed herein.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, solutions suspensions, syrups, wafers, and the like.

Tablets, troches, pills, capsules, and the like may also contain the following: binders such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain the active compound, sucrose or fructose as a sweetening agent, methyl and propylparabens as preservatives, a dye, and flavoring such as cherry or orange flavor. Of course, any material used in preparing any unit dosage form should be pharmaceutically acceptable and substantially non-toxic in the amounts employed. In addition, the compounds of the invention can be incorporated into sustained-release preparations and devices. For example, the compounds can be incorporated into time-release capsules, time-release tablets, and time-release pills. In addition, the compounds can be coated with nanospheres.

The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols or water/alcohol/glycol blends, in which the compounds of the invention can be dissolved or dispersed at effective levels, optionally with the aid of nontoxic surfactants. Adjuvants such as fragrances and additional antimicrobial agents can be added to optimize the properties for a given use.

Useful dosages can be determined by comparing their in vitro activity, and by comparing their in vivo activity in animal models. Methods for the extrapolation of effective dosages in mice and other animals to humans are known to the art.

The amount of the compounds of the invention required for use in treatment will vary with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The attending clinician, taking into account the particulars of the case, will select the particular mode of administration and the dosage regimen. Treatment may involve daily or multi-daily doses of compound(s) over a period of a few days to months, or even years.

The compounds of the invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple oral, rectal and/or intracolonic administration.

The following examples are not intended to limit the scope of the invention in any way.

EXAMPLES

Example 1

Rectal Administration of Cleansing Composition

A cleansing composition including 1.2 mL simethicone (6% w/v), 5 mL acetylcysteine (10% w/v) and 5 mL docusate (1% w/v) sodium in 250 mL tap water is administered in a rectal enema form prior to a colonoscopy. The total volume of composition introduced into the patient is one liter. The patient's colon is sufficiently cleansed, allowing for improved visualization of the colon surface.

Example 2

Administration of Cleansing Composition Using Pump and Catheter

A cleansing composition as in Example 1, including 1.2 mL simethicone, 5 mL acetylcysteine and 5 mL docusate sodium in 250 mL tap water is administered to a patient using a pump and catheter device prior to a colonoscopy. The total

Example 3

Intracolonic Administration of Cleansing Composition

A cleansing composition as in Example 1, including 1.2 mL simethicone, 5 mL acetylcysteine and 5 mL docusate sodium in 250 mL normal saline is administered intracolonically during a colonoscopy. A 60 cc syringe is filled with the composition, and an amount of the composition that is effective to clean the colon as desired is injected via the "working channel" of the colonoscope (e.g., at least one syringe full). The patient's colon is sufficiently cleansed, allowing for improved visualization of the colon surface.

Example 4

Oral Administration of Cleansing Composition

A cleansing composition as in Example 1, including 1.2 mL simethicone, 5 mL acetylcysteine and 5 mL docusate sodium in 250 mL distilled water is administered orally to a patient the day before the patient's colonoscopy. The patient ingests about 500 mL of the composition. The patient's colon is sufficiently cleansed, allowing for improved visualization of the colon surface.

Example 5

Administration of the Composition for Treatment of Constipation

A cleansing composition as in Example 1, including 1.2 mL simethicone, 5 mL acetylcysteine and 5 mL docusate sodium in 250 mL normal saline is administered orally to a patient suffering from constipation. The patient ingests about 250 mL of the composition. The patient's constipation is alleviated.

Example 6

Administration of the Composition for Treatment of Abdominal Discomfort

A cleansing composition as in Example 1, including 1.2 mL simethicone, 5 mL acetylcysteine and 5 mL docusate sodium in 250 mL normal saline is administered orally to a patient suffering from abdominal discomfort. The patient ingests about 250 mL of the composition. The patient's abdominal discomfort is alleviated.

Example 7

Administration of the Composition for Treatment of Gastric Bezoars

A cleansing composition as in Example 1, including 1.2 mL simethicone, 5 mL acetylcysteine and 5 mL docusate sodium in 250 mL normal saline is administered orally to a patient suffering from a gastric bezoar. The patient ingests about 250 mL of the composition as a dosage in a course of treatment. The patient's gastric bezoar is dissolved.

volume of composition introduced into the patient is one liter. The patient's colon is sufficiently cleansed, allowing for improved visualization of the colon surface.

Example 8

Efficacy of Cleansing the Residual Stool and Secretions During Colonoscopy Using a Combination of N-Acetylcysteine, Docusate Sodium and Simethicone—Proof of Concept Study Introduction:

Colonoscopy is a procedure whereby a fiber-optic instrument is introduced into the rectum via the anal canal. The leading end of the instrument is gradually advanced all the way up to the cecum, i.e., the beginning of the colon. When the leading end of the instrument is in the cecum, the actual examination starts. If the cecum is spotlessly clean, its surface is examined in detail for any abnormality, like a growth or a tumor (usually called a polyp). The instrument is then gradually withdrawn through the entire length of the colon. The surface of the colon is washed with water to remove any adherent stool or secretions to assist with detailed examination. This extra cleansing is undertaken during the colonoscopy to avoid missing any small or "flat" growth. Despite best efforts for cleansing the colon prior to doing a colonoscopy, there is always some residual stool and secretions in the colon which pose a hindrance in visualization and careful examination of the surface of the colon. The prevailing practice is generally to wash the residual stool and secretions with water. The water is introduced into the colon by either injecting it down the working channel of the instrument i.e. the colonoscope or by means of a pump with a foot pedal. The water source is connected to the colonoscope by a tubing and water can be introduced into the colon by pushing the foot pedal.

Various studies have used a bowel cleansing score that is determined by colonoscopists as described below. The cleansing is scored on a 4 point scale:

1—poor (large amounts of fecal residue requiring additional cleansing).

2—fair (enough feces or fluid to prevent a completely reliable exam).

3—good (small amounts of feces or fluid, not interfering exam).

4—excellent (no more than small bits of adherent feces/fluid).

The stool residue and dried or liquid intestinal fluid poses difficulty in suctioning as the mucus in the stool makes it adherent to the lining and also more viscous. Using water to dilute the stool and make it less viscous is the only source of colon cleansing that is commonly practiced. In addition to the secretions and solid stool residue there is a varying amount of bubbles in the secretions. The content is often times, thick, viscous and frothy. It is our experience that water does not dissolve the bubbles that easily. One has to keep flushing a large amount of water and continuously suctioning the liquid to get rid of the bubbles. Despite cleaning the colon it is still quite difficult to get rid of the bubbles. Simethicone assists with dissolution of the bubbles in a very efficient manner. The thick mucoid stool is made less viscous by the mucolytic effect of N-acetylcysteine and the docusate assists with softening the effluent which in turn makes it very easy to suction out.

The flexible telescope is inserted within the large bowel, and most of the time the patient is lying on the left side. Sometimes the patient is asked to roll over to make the procedure easier to perform.

Objective: To evaluate the effect of a novel colon cleansing formula for colon cleansing during colonoscopy.

1 Determine the best possible method for cleansing the residual stool and secretions during colonoscopy.

2 Increase efficiency by decreasing the time for colonoscopy.

3 Avoid missing subtle and "flat mucosal lesions" in the colon by achieving a greater degree of colon cleansing.

Methods:

The study population comprises subjects having no symptoms suggestive of colon cancer, having a suggestion of colon cancer, or having comorbidities of all sorts of diseases. The subjects range in age from about 20-90, and have a male to female ratio of about 1:2. The study population is divided into four groups.

Group I Control group (using water for colon cleansing).
Group II Using simethicone in combination with water
Group III Using simethicone and docusate sodium with water.
Group IV Using the combination of simethicone, docusate sodium and N-acetylcysteine with water The strengths of the solutions are described below: The solution is made per liter.

| COMPOUND | STRENGTH | AMOUNT |
| --- | --- | --- |
| N-acetylcysteine | 10% sol (10 g/100 ml) | 20 ml per liter |
| docusate sodium | 100 mg/10 ml | 10 ml per liter |
| simethicone | 60 mg/ml | 10 ml per liter |

Simethicone was used alone and in combination with docusate sodium. The results of this study are indicated below. Similar findings are expected from a larger, confirmative study. Furthermore, it is expected that the addition of N-acetylcysteine to the simethicone plus docusate sodium solution will provide the same degree of cleansing, or more, than the solution without the N-acetylcysteine. Furthermore, it is expected that any combination of two or more of these three components will provide efficient cleansing of the colon. For example, the docusate is expected to decrease the amount of work by about 33-50%.

Results: The efficacy of the product was deduced by comparing the ease of colonoscopy by:

A) Reduction of withdrawal time on colonoscopies done on each individual control group.
B) Ease of removal of effluent/stool debris
C) Tolerability in patients
D) Delta rate of polyp detection Efficacy in:

Group I: The withdrawal time was prolonged especially in patients with class I (poor) cleansing. There is a higher chance to miss sessile lesions. This is the group which stands to benefit the most. All components of the solution are active in this group. Studies of various types of preparations for colonoscopy show that about 15% of patients will have this type of an outcome. As the preparation improves the need for further cleansing decreases.

Group II: Simethicone makes it significantly easy to remove all bubbles especially from the cecum. This is on account of the location of the cecum. The secretions from the small intestine drop into the colon. The beginning of the colon is the cecum. Due to continuous pouring of secretions into the cecum, it is invariably coated with wet or dried secretions. Also the most amount of bubbles are in the cecum. The bubbles are on account of the bile. Bilious secretions are continuously pouring into the cecum. The most amount of time is spent in cleaning the cecum.

Group III: We noted a significant ease with which the effluent was suctioned out. Addition of docusate made a significant difference. The suctioning time was considerably reduced by the addition of docusate Group IV: We expect that this will be the most efficient model. The bubbles are addressed by simethicone, stool consistency is addressed by colace and N-acetylcysteine by virtue of its mucolytic properties assists in efficient shredding and fragmentation of the stool, thereby greatly facilitating the suctioning the stool.

CONCLUSION

The combination of simethicone and docusate sodium works well and assists in a more efficient cleaning of the colon that, for example, simethicone alone, or water. Simethicone works as an excellent agent to remove all the gas bubbles from the stool. The instillation of docusate changes the stool consistency as such that it is considerably easy to aspirate and the removal becomes more efficient and less time consuming.

From the foregoing and subsequent description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. Provisional Application 61/255,344, filed Oct. 14, 2009, and in the figures, are hereby incorporated in their entirety by reference. More particularly, portions of the references are incorporated by reference with respect to the method or finding for which they are cited.

I claim:

1. A method for cleansing the colon of a subject during a colonoscopy screening procedure, comprising during the colonoscopy introducing into the lumen of the colon of the subject, through a channel in a colonoscope, a liquid form of a composition comprising:
   a) N-acetylcysteine and one or both of
   b) simethicone or
   c) a docusate salt,
   wherein the amounts of a), b) and c), are effective, when administered through a colonoscope, in two or fewer flushes, to cleanse stool from the colon of the subject such that a region of the colon in the visual field of the colonoscope contains substantially no adherent stool or intestinal secretions, and
   wherein the concentrations of a), b) and c) are
   a) N-acetylcysteine: from about 20 mg to 20 g/L,
   b) simethicone: from about 3 mg to 3 g/L,
   c) a docusate salt: from about 2 mg to 2 g/L.

2. The method of claim 1, wherein the composition comprises N-acetylcysteine and simethicone and a docusate salt.

3. The method of claim 1, wherein introduction into the lumen of the colon through the colonoscope comprises
   operating a pump which is operably linked via a conduit to a container that comprises the composition comprising
   a) N-acetylcysteine and one or both of
   b) simethicone, or
   c) a docusate salt,
wherein the amounts of a), b) and c), are effective, when administered through a colonoscope, in two or fewer flushes, to cleanse stool from the colon of the subject such that a region of the colon in the visual field of the colonoscope contains substantially no adherent stool or intestinal secretions, allowing inflow of the composition from the container to the pump, and is also operably linked via a channel to a colonoscope, allowing outflow of the composition from the pump to the channel in the colonoscope, thereby administering the composition to the lumen of the colon.

4. The method of claim 1, wherein introduction into the lumen of the colon through the colonoscope comprises introducing, with a syringe, the composition comprising
a) N-acetylcysteine and one or both of
b) simethicone, or
c) a docusate salt, wherein the amounts of a), b) and c), are effective, when administered through a colonoscope, in two or fewer flushes, to cleanse stool from the colon of the subject such that a region of the colon in the visual field of the colonoscope contains substantially no adherent stool or intestinal secretions into a channel in the colonoscope,
thereby administering the composition to the subject.

5. The method of claim 1, wherein the N-acetylcysteine is in an amount of about 2 g/L.

* * * * *